United States Patent
Kühner (10) Patent No.: US 7,993,339 B2
(45) Date of Patent: Aug. 9, 2011

(54) APPARATUS FOR ARGON-PLASMA COAGULATION

(75) Inventor: Ralf Kühner, Stuttgart (DE)

(73) Assignee: ERBE Elektromedizin GmbH, Tübingen (DE)

( * ) Notice: Subject to any disclaimer, the term of this patent is extended or adjusted under 35 U.S.C. 154(b) by 892 days.

(21) Appl. No.: 11/570,086

(22) PCT Filed: May 19, 2005

(86) PCT No.: PCT/EP2005/005454
§ 371 (c)(1),
(2), (4) Date: Dec. 6, 2006

(87) PCT Pub. No.: WO2005/120372
PCT Pub. Date: Dec. 22, 2005

(65) Prior Publication Data
US 2007/0225700 A1    Sep. 27, 2007

(30) Foreign Application Priority Data

Jun. 11, 2004 (DE) .......................... 10 2004 028 362
Jul. 14, 2004 (DE) .......................... 10 2004 033 975

(51) Int. Cl.
*A61B 18/14* (2006.01)
(52) U.S. Cl. .......................................... 606/49; 606/40
(58) Field of Classification Search ............... 606/32–52
See application file for complete search history.

(56) References Cited

U.S. PATENT DOCUMENTS

| 2,936,183 | A | * | 5/1960 | Basham ................... 137/614.05 |
| 4,299,226 | A | * | 11/1981 | Banka ........................... 604/509 |
| 4,541,457 | A | * | 9/1985 | Blenkush ................. 137/614.06 |
| 4,946,455 | A | * | 8/1990 | Rosen ........................... 604/403 |
| 5,201,899 | A | | 4/1993 | Austin, Jr. et al. |
| 5,207,672 | A | | 5/1993 | Roth et al. |
| 5,244,462 | A | | 9/1993 | Delahuerga et al. |
| 5,720,745 | A | * | 2/1998 | Farin et al. ........................ 606/49 |
| 5,749,889 | A | * | 5/1998 | Bacich et al. ................... 606/198 |
| 6,602,249 | B1 | | 8/2003 | Stoddard et al. |
| 2001/0018587 | A1 | | 8/2001 | Yamamoto |
| 2003/0083628 | A1 | | 5/2003 | Blanco |
| 2003/0105458 | A1 | | 6/2003 | Platt |
| 2005/0171528 | A1 | * | 8/2005 | Sartor et al. ..................... 606/41 |

FOREIGN PATENT DOCUMENTS

| DE | 10228791 A1 | 1/2004 |
| EP | 0633790 B1 | 5/2000 |
| EP | 1 090 597 A1 | 4/2001 |
| FR | 2657489 A1 | 7/1991 |
| JP | 3-146068 A | 6/1991 |
| JP | 5-184609 A | 7/1993 |

(Continued)

*Primary Examiner* — Michael Peffley
(74) *Attorney, Agent, or Firm* — Dickstein Shapiro LLP (57) ABSTRACT

The invention relates to an apparatus for argon-plasma coagulation in which working gas is supplied to a tissue that is to be treated by passage through gas-supply devices (20) in a supply-flow direction, and the working gas flows out of a distal end of the gas-supply devices. This apparatus for argon-plasma coagulation is further developed with the aim of preventing contamination of the gas-supply devices by working gas, bodily gases and/or bodily liquids. For this purpose at least one obstructor (30) is provided, which is or can be connected to the gas-supply devices and serves to obstruct a flow of gas and/or liquid into the gas-supply devices, against a supply-flow direction.

13 Claims, 4 Drawing Sheets

FOREIGN PATENT DOCUMENTS

| | | |
|---|---|---|
| JP | 2000-107196 A | 4/2000 |
| JP | 2001-145633 A | 5/2001 |
| JP | 2006-501943 A | 1/2006 |
| WO | WO 03080166 A1 * | 10/2003 |
| WO | WO 2004/033004 A1 | 4/2004 |

* cited by examiner

APPARATUS FOR ARGON-PLASMA COAGULATION

CROSS-REFERENCE TO RELATED APPLICATIONS

This application is a Section 371 of International Application No. PCT/EP2005/005454, filed May 19, 2005, which was published in the German language on Dec. 22, 2005, under International Publication No. WO/2005/120372 A1, the disclosure of which is incorporated herein by reference.

BACKGROUND OF THE INVENTION

The invention relates to an apparatus for argon-plasma coagulation (APC).

High-frequency surgery, of which argon-plasma coagulation forms a subcategory, has been employed for many years in both human and veterinary medicine in order to coagulate and/or cut biological tissue. In this process, by means of suitable electrosurgical instruments high-frequency current is conducted through the tissue to be treated, so that this tissue is altered by protein coagulation and dehydration. Therefore a coagulation process can serve to close vessels and stop bleeding. A cutting process subsequent to the coagulation process then enables previously coagulated tissue to be completely separated from the remaining tissue.

Argon-plasma coagulation enables non-contact coagulation of tissue and serves for effective stanching of blood and devitalization of tissue. In this kind of coagulation an inert working gas, e.g. argon, is conducted through gas-supply devices from an argon-plasma-coagulation instrument, which determines the argon dosage and monitors for errors, to the tissue that is to be treated. The working gas can then be used to generate a plasma stream between a distal end of the gas-supply devices, e.g. a probe, and the tissue. The HF current can then be applied to the tissue to be treated without bringing the electrosurgical instrument into contact with the tissue. Hence the possibility of the tissue adhering to the instruments is avoided. The argon-plasma coagulation additionally prevents carbonization of the tissue as well as smoke formation and unpleasant odors.

The technique of argon-plasma coagulation can be employed both with an opened body and also by minimally invasive means. In the latter application the probe to supply the working gas is pushed into the body, e.g. through an endoscope, along a route through a natural body opening until it reaches the operation site in the relevant body cavity.

A disadvantage of known forms of APC apparatus and their probes resides in the fact that during insertion of the probe into the body cavity or after a probe has already been inserted, from a distal end of the probe it is possible for the working gas, as well as gases and/or liquids originating within the body, to flow back into the gas-supply devices. In this case the probe itself, but also elements of the apparatus for argon-plasma coagulation connected thereto, such as the APC instrument, become contaminated.

Therefore some of the known forms of apparatus provide sterile, hydrophobic membrane filters that are preferably positioned at a distal end of the gas-supply devices, i.e. in particular in the probe, and are intended to prevent reflux of gases and/or liquids. However, such filters are expensive, must be exchanged at regular intervals, and therefore require an enormous amount of maintenance and cost a great deal. Furthermore there is a risk of forgetting to exchange the filter, so that a subsequent operation will be carried out with a contaminated appliance. Once an appliance has been contaminated, it can no longer be reliably prepared for further use.

As an alternative, the known appliances provide for the working gas to flow continuously through the probe to the tissue to be treated. This likewise avoids backward flow. However, prolonged inflow for hygienic purposes floods the affected body cavity unnecessarily with the inert working gas, which can easily lead to complications during the operation. In addition, the whole APC apparatus must already be in operation when the probe is inserted, to ensure the flow of gas. And both appliance and gas flow must be switched on continuously, until the probe has been completely removed from the body cavity.

BRIEF SUMMARY OF THE INVENTION

The present invention provides an apparatus for argon-plasma coagulation which is intended to prevent contamination of the gas-supply devices and/or the argon-plasma coagulation instrument with working gas as well as bodily gases and/or bodily liquids.

In particular, according to the present invention there is provided an apparatus for argon-plasma coagulation in which working gas is supplied to a tissue to be treated by means of gas-supply devices through which the gas flows in a supply-flow direction, and from the distal end of which the working gas emerges. At least one obstructor that is or can be connected to the gas-supply devices is provided, so as to prevent a flow of gas and/or liquids into the gas-supply devices, against the supply-flow direction.

In the invention the gas-supply devices are constructed in such a way as to prevent retrograde flow of working gas as well as bodily gases and/or bodily liquids into the gas-supply devices. For this purpose the gas-supply devices comprise reflux-preventing elements that do not require either to be exchanged or to be separately cleaned.

In a first preferred embodiment the reflux obstructor is or can be attached to a tube, a tubular probe or similar surgical instrument associated with the gas-supply devices. In particular, in this case it is advantageous for the obstructor to be disposed at a distal end of the surgical instrument, for instance the probe, because any kind of gas and/or liquid reflux from the operation region is prevented at an early stage. Only very little of the contaminating gases and/or liquids can penetrate into the probe, because the only volume available extends from the distal end of the probe to the obstructor positioned immediately behind that end. The rest of the probe lumen, as well as other elements of the gas-supply devices that are attached to the probe, remain uncontaminated, which considerably facilitates their cleaning and sterilization.

Another advantage provided by positioning the obstructor at the distal end of the probe is that gas within the probe, in particular working gas, cannot flow out of the APC device when the latter is in the non-activated state. As a result, once the probe has been filled with working gas it can be put into operation more rapidly, which increases its operational reliability.

In another preferred embodiment the obstructor is or can be connected to a connector piece of the surgical instrument of the gas-supply devices. Surgical instruments such as probes often comprise explicitly designed connector pieces, for example explicit probe inserts. When the obstructor is provided within the connector piece, in particular additional elements of the gas-supply devices that are connected to the connector piece can be reliably protected from contamination.

In one preferred embodiment the obstructor is or can be connected to connector conduits by way of which the surgical instrument is connected to an argon-plasma-coagulation instrument of the device for argon-plasma coagulation. Preferably the arrangement is provided in the connector conduits as supplementary measures, i.e. as supplementary obstructor, so as further to increase not only the protection of the connector conduits but also, in particular, the protection of the APC instrument against the inward flow of working gas as well as bodily gases and/or bodily liquids.

The obstructor advantageously is or can be connected to a gas-connector piece disposed on the argon-plasma-coagulation instrument. Thus the APC instrument in particular is reliably protected from retrograde inflow of gases or liquids. It is particularly desirable for the obstructor to be disposed directly on the APC instrument when the connector conduits and/or the surgical instrument, e.g. the probe, are supplied as single-use articles, so that to incorporate the obstructor into them would prove too expensive. However, the obstructor provided on the gas-connector piece is also suitable to protect in particular the APC instrument separately and reliably, in which case the probe and the connector conduits can comprise a corresponding obstructor.

One solution in accordance with the invention provides for an obstructor in the form of a mechanically and/or electrically actuatable device. Mechanically and/or electrically actuatable obstructors are commercially available, economical components such as valves, which can be connected at the desired site in a simple manner. The mechanically and/or electrically actuatable device then makes it possible to control a flow direction and an amount of gas in the simplest manner, at a desired point in time.

The obstructor is advantageously constructed as a shut-off valve, for instance a non-return valve. Non-return valves are simple and economical structural components that reliably prevent retrograde flow of working gas, bodily gases and/or bodily liquids. Furthermore, a valve of this kind serves as a seal in both directions in case no surgical instrument, e.g. the probe, is attached to the APC device. Thus, e.g., an emergence of residual gas from the connector conduits can be avoided, even when their end that would ordinarily accommodate the probe is open. Non-return valves are especially suitable for installation in those elements of the apparatus for argon-plasma coagulation that must repeatedly prepared and accordingly should be inserted several times. Non-return valves can comprise conical, spherical or plate elements, which in each case is opened by a pressure exerted by a gas or liquid, which acts, e.g., against a spring force. When a force is applied to the element in the shut-off direction, the spring force is supplemented by the force the pressure exerts on the valve seating, so that the valve blocks the flow. Non-return valves or similar shut-off valves can, however, also be actuated manually, for example by way of a stop-cock wheel or rotating handle.

In one preferred embodiment the shut-off valve is constructed as a lip seal, i.e. as a duckbill valve. The lip seal is advantageously configured so that the lips open when the working gas is flowing in the supply-flow direction, whereas in case of reflux of working gas, bodily gases and/or bodily liquids, the lips close in accordance with their construction. The resistance that lip seals present to flow in the supply direction is not appreciable, but closure in the opposite direction is reliable. The lip seal is especially suitable for placement in the lumen of the probe.

Alternatively or in addition at least one throttle valve can be connected within the gas-supply devices. The throttle valve is designed as an adjustable resistance and influences the volume flow in such a way that a gas or liquid must exert a particular degree of pressure before being able to flow through the valve. Then the valve can be set, for example, such that to open the valve the gas pressure exerted by the working gas in the supply direction is required. A retrograde flow of working gas, bodily gases and/or bodily liquids, on the other hand, does not reach this required pressure because the flow velocity is too low, so that the valve blocks flow directed against the supply direction. Here the supply direction is defined as the direction of gas flow from the APC instrument to the operation region. A throttle-type non-return valve would fundamentally prevent retrograde flow independently of the pressure.

Preferably the obstructor can be opened by an actuation means that is or can be connected to an element of the gas-supply devices disposed in a direction opposite to the supply direction and thus ahead of an element comprising the obstructor, so that opening of the obstructor is brought about by connecting the two elements.

Often the surgical instrument, e.g. the probe, is guided to the operation region through a working channel of an endoscope, without the instrument being connected to the APC instrument by way of the connector devices. Because of a pressure difference between body cavity and gas-supply devices, working gas, bodily gases and/or bodily liquids can penetrate into the probe. In order to avoid this, the obstructor that prevents reflux and can be opened by an explicit actuation means is provided within the instrument. If the element comprising the obstructor is connected to the element comprising the actuation means, obstructor and actuation means can cooperate in such a way that the obstructor is opened in the supply direction of flow, by means of the actuation means. Thus, with no great effort, a free path is provided for the working gas to flow in the supply direction.

Preferably the actuation means projects out of the element of the gas-supply devices with which it is associated. Connection to the element comprising the obstructor then necessarily results in contact between obstructor and actuation means, so that the obstructor is actuated, i.e. opened. Opening is brought about, for example, because when connected to elements of the gas-supply devices the projecting actuation means penetrates into the obstructor so as to bore through it, producing an opening that enables gas to flow in the supply direction.

On the other hand, if the actuation means is entirely enclosed within the associated element of the gas-supply devices, then the element comprising the obstructor is to be inserted into the element comprising the actuation means in such a way that a cooperation of actuation means and obstructor is thereby made possible.

Alternatively it is possible not to bore through the obstructor but rather, with the help of the projecting actuation means, to shift at least parts of the obstructor out of a first position, in which the obstructor is kept in a closed state, into a second position in which the obstructor is kept in an opened state.

In one preferred embodiment the obstructor is constructed as an element that can be irreversibly opened by the actuation means. The irreversibly openable element is preferably designed as membrane. A membrane is an extremely economical component and therefore should preferably be employed for single-use probes. While the probe is being introduced into the body cavity, the membrane on one hand prevents bodily gases and/or bodily liquids from flowing in, so that the probe as well as any connector conduits that are present do not become contaminated. On the other hand, it is easy for an appropriately designed actuation means to bore through the membrane.

In another preferred embodiment the obstructor is constructed as an element that can be opened several times by the actuation means. An element suitable for multiple opening is in particular a membrane with a specified opening site, i.e. a preformed opening site, which nevertheless is nearly impermeable to gases and/or liquids as long as no boring has occurred. When a hole is bored in the membrane at the specified opening site, at least parts of the membrane give way elastically to the actuation means, enabling the working gas to flow through. When the actuation means is removed, the parts of the membrane resume their original position, i.e. the membrane is again closed. Because the parts of the membrane that give way are then in close contact with the actuation means, the actuation means should be constructed as a projecting hollow body. Thus flow of the working gas through the hollow body is ensured.

The elastic membrane can also be constructed so that working gas flowing in the supply direction causes the membrane to open because of the pressure the working gas exerts, whereas a retrograde flow of working gas, bodily gases and/or bodily liquids does not exert sufficient pressure to cause the membrane to open.

Preferably the multiply openable element is constructed as an obstructor with a body that obstructs the flow of gas and/or liquid and can be linearly shifted by the actuation means. The body is, for example, connected to a spring element so that the actuation means pushes the body against the spring force and thus frees a flow path for the working gas. When the actuation means is removed, the spring element returns the body to its original, starting position, so that the obstructor is again impermeable to the retrograde flow of working gas, bodily gases and/or bodily liquids. The arrangement described here is an extremely reliable possible way to prevent retrograde flow practically completely. The arrangement is particularly suitable for re-usable elements of the gas-supply devices.

In one preferred embodiment the actuation means is constructed as a spike, cannula or plunger. A plunger provides an economical component in particular for the multiply openable obstructor that cooperates with the actuation means, whereas cannulas or spikes are provided primarily for boring through the membrane. When a cannula is used, the flow of the working gas is additionally ensured by the passage in the cannula. The actuation means designed as plunger, cannula or spike can be attached in a simple manner within the element of the gas-supply devices provided for that purpose, and can be replaced whenever required.

Alternatively it is possible for the actuation means to be made integral with the element of the gas-supply devices. The distal end of the element is then, e.g., beveled or constructed like a plunger. This simplifies manipulation, and at the same time the costs of manufacture can be reduced.

It is also possible to make the actuation means itself so that it can be actuated; for instance, connection of the relevant elements of the gas-supply devices triggers a mechanism that moves the actuation means in the direction of the obstructor and thereby causes the latter to open. The mechanism in this case could be constructed, e.g., as a spring mechanism.

In another preferred embodiment it is provided that the obstructor comprises a guarantee closure. This is particularly desirable for single-use probes, in which such identification guarantees an intact obstructor.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 3b is a side elevation of a distal end of an element of gas-supply devices, designed to cooperate with the element shown in FIG. 3a.

FIG. 4b is side elevation of a distal end of an element of gas-supply devices, designed to cooperate with the element shown in FIG. 4a.

DETAILED DESCRIPTION OF THE INVENTION

In the following description, the same reference numerals are used for identical parts or parts with identical actions.

Figure 1:
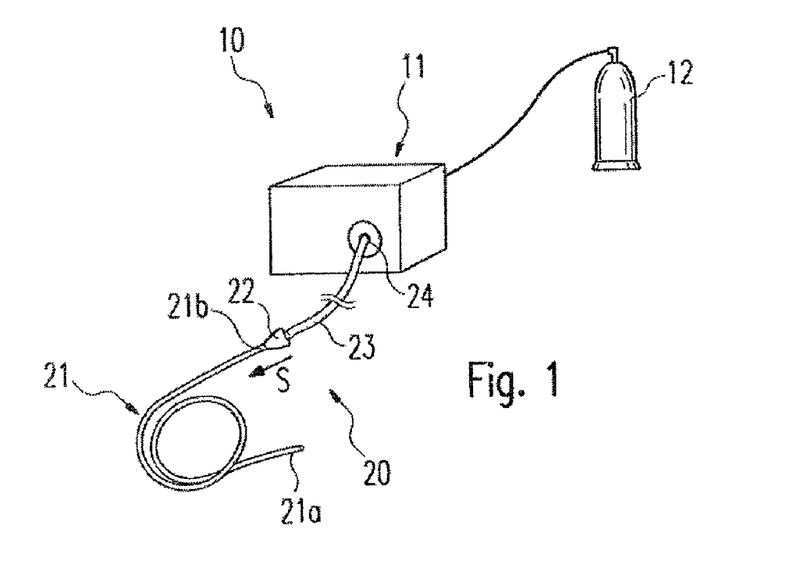
FIG. 1 is a schematic illustration of an apparatus for argon-plasma coagulation according to the present invention.

FIG. 1 shows a schematic representation in perspective of an apparatus for argon-plasma coagulation 10. Here a gas source 12 is connected to an argon-plasma-coagulation instrument 11. The gas source 12 supplies the argon, or similar inert working gas, that is needed for argon-plasma coagulation. The APC instrument 11, which controls the gas dosage and monitors for errors, comprises a gas-connector piece 24 by way of which a first end of a connecting conduit 23 is connected to the APC instrument 11. A second end of the connecting conduit 23 is joined to a surgical instrument, here a probe 21, by way of a probe insert 22. Alternatively, it is possible for the probe 21 to be connected to the APC instrument 11 directly, by way of the probe insert 22. It is likewise possible for the probe 21 to be joined to the connector conduit 23 by way of a screw junction. The gas connector piece 24, the connector conduit 23, the probe insert 22 and the probe 21 constitute gas-supply devices 20 of the APC apparatus 10. The probe 21 comprises an electrode (not shown) to supply a high-frequency current to the operation region, said current being provided by a HF generator (not shown). It is possible to construct the HF generator so that it is integral with the APC instrument 11.

The argon-plasma coagulation can be carried out both with the body opened and also by a minimally invasive route. For a minimally invasive operation the probe 21 shown in FIG. 1 is customarily pushed through an endoscope (not shown) by way of a natural body opening into an appropriate body cavity until it reaches the operation region. Working gas flows to the operation site from a distal end 21a of the probe 21, so that an argon-plasma stream is generated between the probe 21 and a tissue that is to be treated. Because of the plasma, the electrical current can be applied to the tissue with no contact between instrument and tissue, by way of the ionized working gas.

To prevent the working gas, bodily gases and/or bodily liquids such as blood or other liquids originating in the tissue from flowing back into the gas-supply devices 20, the latter according to the present invention comprise at least one obstructor (not shown in FIG. 1) to block this reflux. The obstructor is or can be connected within at least one element of the gas-supply devices 20. Thus the obstructor is provided at least at the surgical instrument, e.g. at the probe 21, so as to prevent the reflux at as early a stage as possible. If the connecting conduits 23 and/or the probe insert 22 comprise an obstructor, the connecting conduits are in addition protected from contamination. In particular, however, the obstructor should also be disposed in or at the gas-connector piece 24 of the APC instrument 11, so as to avoid contamination precisely here.

Figure 2:
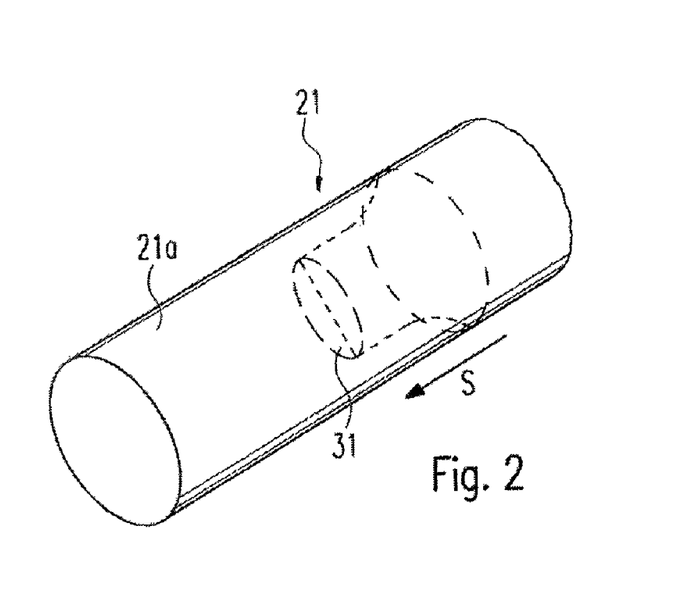
FIG. 2 is a perspective view of a distal end of an element of gas-supply devices with an obstructor in a first embodiment of the invention.

FIG. 2 shows in perspective an element of gas-supply devices 20, for example a distal end 21a of a probe 21 with an obstructor. The obstructor here is designed as a lip seal 31. Lip seals are also termed duckbill valves. The lip seal 31 can be opened in a desired direction of supply flow S of the working gas, namely in the direction from the APC instrument 11 to the operation region, whereas if there is backward flow of working gas, bodily gases and/or bodily liquids, it closes according to the nature of its construction.

In the place of the lip seal 31 any desired kind of valve, in particular shut-off valves, can be incorporated into an element of the gas-supply devices. These reliably prevent retrograde flow, so that contamination of the gas-supply devices 20 is avoided. Throttle or throttle-non-return valves can also be installed for reliable prevention of reflux, preferably in gas-supply devices 20 designed for multiple use. The throttle valve is constructed as an adjustable resistance and influences the volume flow in such a way that it does not permit flow in the supply direction until a particular pressure is being exerted by a gas or a liquid. Then the valve can for example be set so that in order for it to open, the pressure exerted by the working gas in the supply-flow direction is required. A retrograde flow of working gas, bodily gases and/or bodily liquids, in contrast, does not reach this required pressure because it is flowing too slowly, so that the valve blocks flow against the supply direction.

Figure 3A:
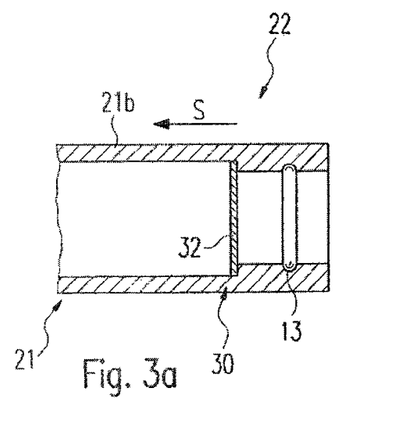
FIG. 3a is a sectional view of a proximal end of an element of gas-supply devices with an obstructor in a second embodiment of the invention.
Figure 3B:
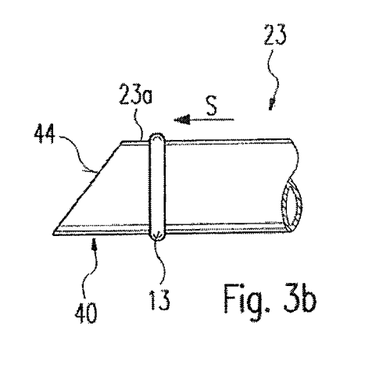

FIG. 3a shows a sectional view of an element of gas-supply devices 20, for example a proximal end 21b of a probe 21 with an obstructor 30. The proximal end 21b comprises in practical application a connector piece, i.e. in this case a probe insert 22. The latter is constructed according to FIG. 3a with a membrane 32 as obstructor. FIG. 3b shows an actuation means 40 in the form of the distal end of an element of gas-supply devices 20, e.g. a distal end 23a of a connector conduit 23 to join the probe 21 to the APC instrument 11; this element is designed to cooperate with the element shown in FIG. 3a. The actuation means 40 has a beveled end 44 and is configured so that it can be introduced into the proximal end 21b of the probe 21, i.e. into the probe insert 22. As soon as probe 21 and connector conduit 23 are joined together, the distal end 23a of the connector conduit 23 bores through the membrane 32 because of the beveled part 44, and opens up a route for a working gas to flow in the supply direction S, from the APC instrument 11 to the operation region.

Alternatively it is possible for FIG. 3b to comprise a cannula, which for example is explicitly provided at or in a connector conduit and acts according to the above description.

The cooperation of two elements of the gas-supply devices 20 that can be joined to one another, i.e. the cooperation of the obstructor 30 with the actuation means 40 to open the obstructor 30, represents an extremely simple and economical possibility for freeing a flow path only in the desired supply direction S. This is advantageous in particular when the surgical instrument, e.g. the probe 21, should be guided into the relevant body cavity without being joined to the APC instrument 11. Because of a pressure difference between body cavity and gas-supply devices, gases and/or liquids can easily penetrate into the probe 21. The obstructor 30 is therefore constructed in such a way that on one hand the penetration of contaminating substances is prevented, while on the other hand it is possible to open it by the complementary actuation means 40.

Figure 4A:
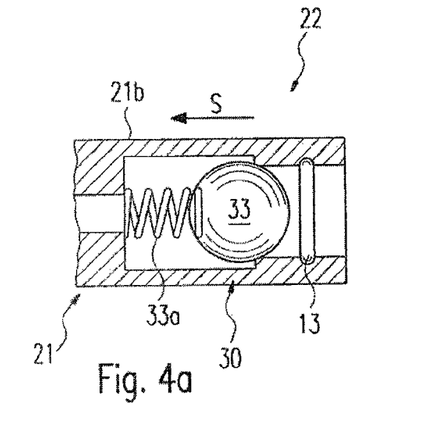
FIG. 4a is a sectional view of a proximal end of an element of gas-supply devices with an obstructor in a fourth embodiment of the invention.
Figure 4B:
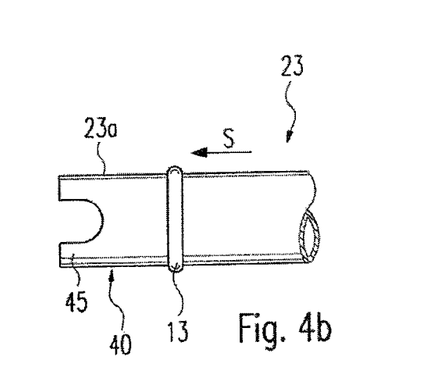

FIG. 4a likewise shows a sectional view of a proximal end of an element of gas-supply devices 20, for example a proximal end 21b of a probe 21, i.e. a probe insert 22, with an obstructor 30. Here a spherical body of the obstructor 30 disposed in the insert 22 obstructs the flow of gas and/or liquid both in a supply direction S of the APC instrument 11, i.e. in the direction toward the operation region, as well as against that direction. The spherical body 33 in this exemplary embodiment is constructed with a spring element 33a. FIG. 4b shows a distal end of an element of gas-supply devices, e.g. a distal end 23a of a connector conduit 23 for joining the probe 21 to the APC instrument 11, this element being designed to cooperate with the element according to FIG. 4a. An actuation means 40 complementary to the obstructor 30 is made integral with the connector conduit 23. As shown in FIG. 4b, the actuation means 40 and hence the connector conduit 23 comprises a plunger-like end 45.

As the two elements, the probe 21 and the connector conduit 23, are being joined together, the actuation means 40 with the plunger-shaped end 45 counteracts a spring force associated with the spring element 33a by pressing against the spherical body 33 and thus moving it in the supply-flow direction S, out of its blocking position into an opening position. This frees the route for flow of the working gas that is needed at the operation region. As long as the working gas flows to the operation region, a retrograde flow of working gas, bodily gases and/or bodily liquids is prevented. When the actuation means 40 is removed, the spring element 33a returns the spherical body 33 into its blocking position, so that the obstructor 30 again obstructs flow both in and against the supply direction S.

Alternatively it is possible for FIG. 4b to show a cannula with a plunger-shaped end, which for example is explicitly provided at or in a connector conduit and acts according to the above description.

As shown in FIGS. 3a, 3b and 4a, 4b, the elements of the gas-supply devices 20 can be joined to one another by plugging them together. For this purpose both the elements comprising the obstructors 30 and the elements comprising the actuation means 40 also comprise stopping elements 13, that limit the depth to which the distal end 23a of the connector conduits 23 can penetrate into the proximal end 21b of the probe 21, i.e. into the probe insert 22. Alternatively, it is also possible here for a screw connection to be provided, in which the respective elements are provided with screw thread and counterpart thread.

Figure 5:
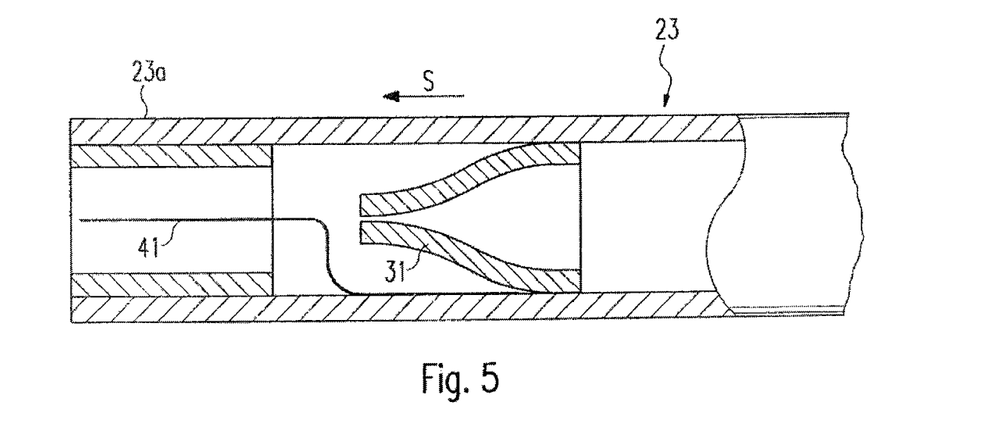
FIG. 5 is a sectional view of a proximal end of an element of gas-supply devices with an obstructor and an actuation means in a fifth embodiment of the invention.

FIG. 5 shows a sectional view of a distal end of an element of gas-supply devices, e.g. a distal end 23a of a connector conduit 23, with an obstructor and an actuation means. In the connector conduit 23 is provided a lip seal 31 such as has been described above. In addition the connector conduit 23 comprises a spike 41 as actuation means for an element of the gas-supply devices 20 that is downstream in the supply-flow direction S. The spike 41 is formed completely within the connector conduit 23, so that an element of the gas-supply devices that comprises the obstructor can be inserted into the element comprising the actuation means in such a way that it becomes possible for the actuation means and obstructor to cooperate with one another.

Figure 6:
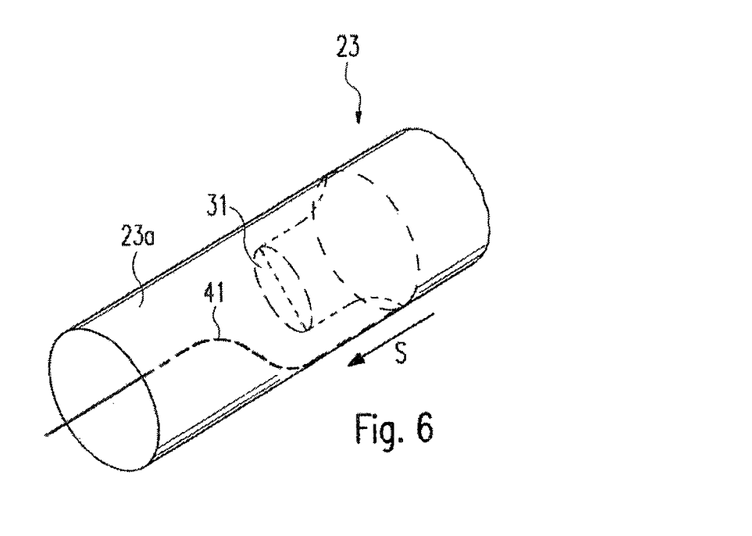
FIG. 6 is a perspective view of a distal end of an element of gas-supply devices with an obstructor and an actuation means in a sixth embodiment of the invention.

FIG. 6 shows an exemplary embodiment similar to that in FIG. 5, but in perspective. The element following the actuation means, for example a probe, would then in both exemplary embodiments be constructed with an obstructor such as a membrane that can be opened by the spike 41. When connector conduit and probe are pushed together, the membrane would be pierced by the spike 41 in a manner like that described under FIGS. 3a and 3b.

Figure 7A:
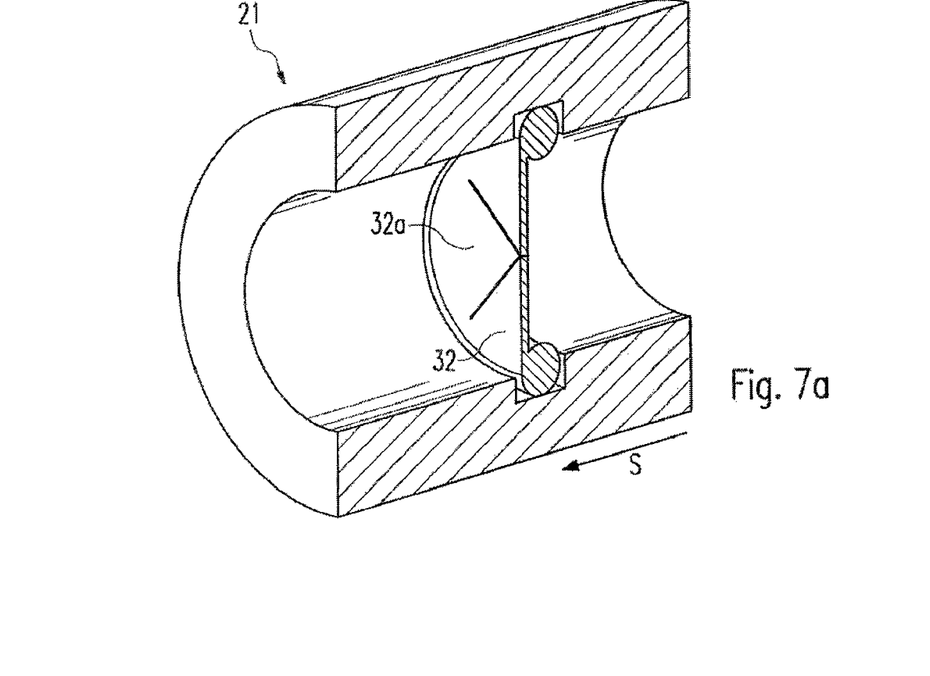
FIG. 7a is a perspective sectional view of an obstructor in an element of a gas-supply device in a seventh embodiment of the invention.

FIG. 7a shows a perspective sectional view of an obstructor in an element of gas-supply devices, for example in a probe 21. The obstructor here has the form of an elastic membrane 32, which comprises a specific opening site, i.e. a preformed opening site 32a. In the closed state, the membrane 32 is nearly impermeable to gases and/or liquids.

Figure 7B:
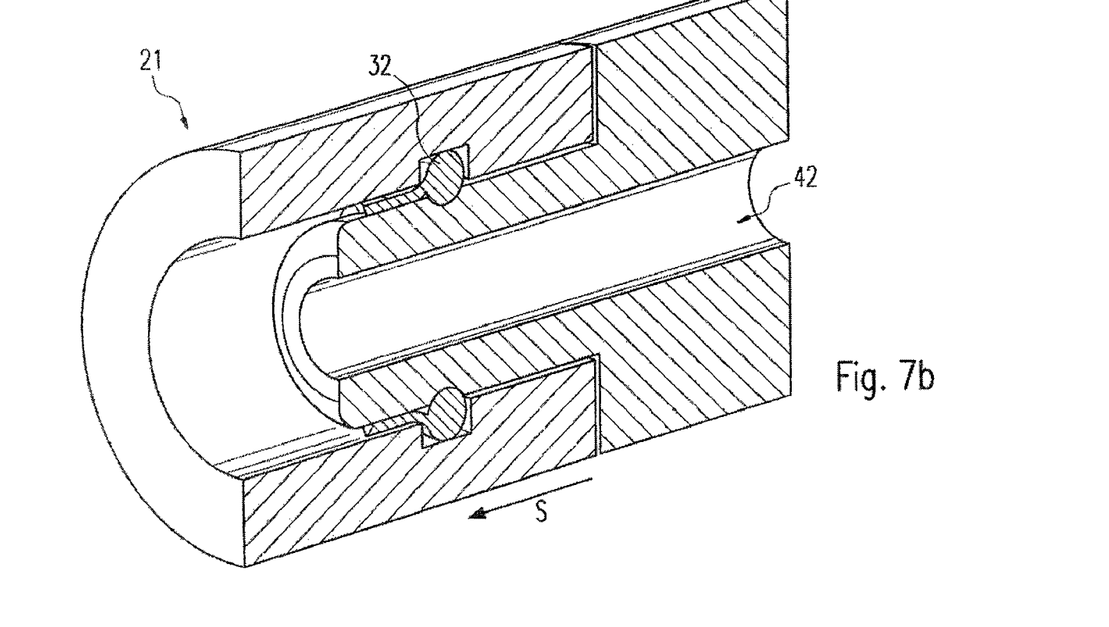
FIG. 7b is a perspective view of the obstructor shown in FIG. 7a in an actuated state.

FIG. 7b shows a perspective view of the obstructor according to FIG. 7a in the actuated state. Here a cannula 42 is provided as actuation means. The cannula 42 can for example be provided at or in a connector conduit (not shown here). As it bores through the membrane 32 at the opening site 32a provided for the purpose, at least parts of the membrane 32 are elastically deflected by the cannula 42. When the cannula 42 is removed, the parts of the membrane 32 return to their original position; i.e., the membrane 32 is again closed. As shown in FIG. 7b, the deflected parts of the membrane 32 are closely apposed to an outer surface of the cannula 42, as the working gas is flowing through the cannula 42.

The elastic membrane 32 can also be constructed in such a way that the working gas flowing in the supply direction S exerts enough pressure to open the membrane 32, whereas the pressure exerted by a retrograde flow of working gas, bodily gases and/or bodily liquids is insufficient to cause opening of the membrane 32. In this case, there is no need for an explicit actuation means such as is shown in FIG. 7b.

It should be pointed out that the obstructors and, where present, complementary actuation means can be provided in any desired elements of the gas-supply devices 20. Especially when a plurality of obstructors are present to prevent reflux of contaminating substances, the elements of the APC apparatus 10 are reliably protected from contamination.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. An apparatus for argon-plasma coagulation that is adapted to supply a working gas to a tissue that is to be treated, said apparatus comprising:
    a gas-supply device through which the working gas flows in a supply-flow direction and from which the working gas flows out at a distal end of the gas-supply device, the gas-supply device comprising a connector conduit, wherein a first end of the connector conduit is connected to an argon-plasma-coagulation instrument and a second end of the connector conduit is joined to a surgical instrument via an insert piece;
    an obstructor disposed in the insert piece, wherein the obstructor obstructs a flow of at least one of gas and liquid in the gas-supply device, against the supply-flow direction; and
    an actuation means disposed in the connector conduit, upstream of the obstructor relative to the supply-flow direction,
    wherein an open state of the obstructor can be achieved by the actuation means by joining together the surgical instrument and the connector conduit via the insert piece.

2. The apparatus according to claim 1, further comprising at least one additional obstructor, wherein the at least one additional obstructor is disposed in at least one of a tube, a tubular probe and the surgical instrument of the gas-supply device.

3. The apparatus according to claim 2, further comprising at least one additional obstructor, the at least one additional obstructor being disposed in the connector conduit.

4. The apparatus according to claim 1, further comprising a gas-connector piece disposed at the argon-plasma-coagulation instrument and at least one additional obstructor, the at least one additional obstructor being disposed in the gas-connector piece.

5. The apparatus according to claim 1, wherein the obstructor comprises one of a mechanically actuatable device and an electrically actuatable device.

6. The apparatus according to claim 1, wherein the obstructor comprises a shut-off valve.

7. The apparatus according to claim 1, wherein the obstructor comprises a lip seal.

8. The apparatus according to claim 1, wherein the obstructor is irreversibly opened by the actuation means.

9. The apparatus according to claim 8, wherein the irreversibly openable obstructor is a membrane.

10. The apparatus according to claim 1, wherein the obstructor is able to be opened several times by the actuation means.

11. The apparatus according to claim 1, wherein the obstructor comprises a membrane with a specified opening site.

12. The apparatus according to claim 1, wherein the obstructor comprises a body that obstructs the flow of at least one of gas and liquid and that is linearly displaceable by the actuation means.

13. The apparatus according to claim 1, wherein the actuation means comprises one of a spike, cannula and a plunger.

* * * * *